United States Patent
Salahat et al.

(10) Patent No.: US 10,456,027 B2
(45) Date of Patent: Oct. 29, 2019

(54) ARCHITECTURE AND METHOD FOR MAXIMALLY STABLE EXTREMAL REGIONS (MSERS)-BASED EXUDATES DETECTION IN FUNDUS IMAGES FOR DIABETIC RETINOPATHY

(71) Applicant: Khalifa University of Science and Technology, Abu Dhabi (AE)

(72) Inventors: Ehab Najeh Salahat, Abu Dhabi (AE); Hani Hasan Mustafa Saleh, Abu Dhabi (AE); Andrzej Stefan Sluzek, Abu Dhabi (AE); Mahmoud Al-Qutayri, Abu Dhabi (AE); Baker Mohammad, Abu Dhabi (AE); Mohammed Ismail Elnaggar, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 6 days.

(21) Appl. No.: 15/497,302

(22) Filed: Apr. 26, 2017

(65) Prior Publication Data
US 2018/0310817 A1 Nov. 1, 2018

(51) Int. Cl.
*A61B 3/00* (2006.01)
*A61B 3/12* (2006.01)
(Continued)

(52) U.S. Cl.
CPC ............ *A61B 3/0025* (2013.01); *A61B 3/12* (2013.01); *G06T 7/0012* (2013.01); *G06T 7/60* (2013.01);
(Continued)

(58) Field of Classification Search
None
See application file for complete search history.

(56) References Cited

U.S. PATENT DOCUMENTS 7,027,054 B1 4/2006 Cheiky et al.
7,725,484 B2 5/2010 Nistér et al.
(Continued)

OTHER PUBLICATIONS

Refining coarse manual segmentations with stable probability regions, by Laaksonen et al, Iowa research online, Oct. 9, 2015. 2015 Proceedings.*

(Continued)

*Primary Examiner* — Vikkram Bali
(74) *Attorney, Agent, or Firm* — Withrow & Terranova, P.L.L.C.

(57) ABSTRACT

Architecture and a method for maximally stable extremal regions (MSERs)-based detection of exudates in an ocular fundus is disclosed. The architecture includes a communication interface to receive pixels of an ocular fundus image. The architecture further includes processing circuitry that is coupled to the communication interface. The processing circuitry is configured to automatically provide labels for light image regions and dark image regions within the ocular fundus image for a given intensity threshold and find MSERs within the ocular fundus image based on the labels. The architecture also determines MSER regions based on the MSER criteria and then highlights the pixels of the ocular fundus image that are located within MSER regions to indicate the exudates in the ocular fundus. The architecture is further configured to determine MSER ellipses parameters based on MSER regions and MSER criteria and then highlight the locations of the exudates in the ocular fundus.

36 Claims, 9 Drawing Sheets

(51) Int. Cl.
  *G06T 7/00* (2017.01)
  *G06T 7/60* (2017.01)
  *G06T 7/62* (2017.01)
(52) U.S. Cl.
  CPC ............ *G06T 7/62* (2017.01); *A61B 3/0041* (2013.01); *G06K 2209/05* (2013.01); *G06T 2207/30041* (2013.01); *G06T 2207/30101* (2013.01)

(56) References Cited

U.S. PATENT DOCUMENTS

| | | |
|---|---|---|
| 7,813,561 B2 | 10/2010 | Jia et al. |
| 8,265,866 B2 | 9/2012 | Altamura et al. |
| 8,295,604 B2 | 10/2012 | Sakai et al. |
| 8,406,532 B2 | 3/2013 | Wang et al. |
| 8,538,077 B2 | 9/2013 | Zitnick, III |
| 9,053,361 B2 | 6/2015 | Baheti et al. |
| 9,311,555 B2 | 4/2016 | Salahat et al. |
| 9,489,578 B2 | 11/2016 | Salahat et al. |
| 9,600,739 B2 | 3/2017 | Salahat et al. |
| 2014/0212050 A1 | 7/2014 | Zhou et al. |
| 2014/0286579 A1 | 9/2014 | Grujic et al. |
| 2016/0071280 A1 | 3/2016 | Salahat et al. |

OTHER PUBLICATIONS

Agurto, Carla et al., "A Multiscale Optimization Approach to Detect Exudates in the Macula," IEEE Journal of Biomedical and Health Informatics, vol. 18, Issue 4, Jul. 2014, IEEE, pp. 1328-1336.

Agurto, Carla et al., "Multiscale Am-Fm Methods for Diabetic Retinopathy Lesion Detection," IEEE Transactions on Medical Imaging, vol. 29, Issue 2, Feb. 2010, IEEE, pp. 502-512.

Donoser, M. et al., "Efficient Maximally Stable Extremal Region (MSER) Tracking," Proceedings of the 2006 IEEE Computer Society Conference on Computer Vision and Pattern Recognition, Jun. 2006, 8 pages.

Donoser, M. et al., "Shape Guided Maximally Stable Extremal Region (MSER) Tracking," 20th International Conference on Pattern Recognition, Istanbul, Aug. 2010, pp. 1800-1803.

Greenhalgh, J. et al., "Real-Time Detection and Recognition of Road Traffic Signs," IEEE Transactions on Intelligent Transportation Systems, vol. 13, No. 4, Dec. 2012, pp. 1498-1506.

Harangi, Balazs et al., "Detection of Exudates in Fundus Images Using a Markovian Segmentation Model," 36th Annual International Conference of the IEEE Engineering in Medicine and Biology Society (EMBC), Aug. 26-30, 2014, Chicago, IL, USA, IEEE, pp. 130-133.

Hsu, G.-S. et al., "Application-Oriented License Plate Recognition," IEEE Transactions of Vehicular Technology, vol. 62, No. 2, Feb. 2013, pp. 552-561.

Huang, L. et al., "Human Skin Detection in Images by MSER Analysis," 18th IEEE International Conference on Image Processing, Brussels, Sep. 2011, pp. 1257-1260.

Kristensen, Fredrik et al., "Real-Time Extraction of Maximally Stable Extremal Regions on an FPGA," 2007 IEEE International Symposium on Circuits and Systems, May 2007, IEEE, pp. 165-168.

Osareh, Alireza et al., "A Computational-Intelligence-Based Approach for Detection of Exudates in Diabetic Retinopathy Images," IEEE Transactions on Information Technology in Biomedicine, vol. 13, Issue 4, Jul. 2009, IEEE, pp. 535-545.

Patton, Niall et al., "Retinal image analysis: Concepts, applications and potential," Progress in Retinal and Eye Research, vol. 25, 2006, Elsevier Ltd., pp. 99-127.

Riemenschneider, H. et al., "Online Object Recognition by MSER Trajectories," 19th International Conference on Pattern Recognition, Tampa, FL, Dec. 2008, 4 pages.

Sivic, J. et al., "Video Google: A Text Retrieval Approach to Object Matching in Videos," Proceedings of the Ninth IEEE International Conference on Computer Vision, Nice, France, Oct. 13-16, 2003, 8 pages.

Varah, S. et al., "Target Detection and Tracking Using a Parallel Implementation of Maximally Stable Extremal Region," GPU Technology Conference, Canada, Mar. 2013, 28 pages.

Zamberletti, Alessandro et al., "Text Localization based on Fast Feature Pyramids and Multi-resolution Maximally Stable Extremal Regions," ACCV 2014 Workshops Computer Vision, Springer International Publishing, 2014, pp. 91-105.

Zhang, Bob et al., "Detecting Diabetes Mellitus and Non-Proliferative Diabetic Retinopathy using Tongue Color, Texture, and Geometry Features," IEEE Transactions on Biomedical Engineering, vol. 61, Issue 2, Sep. 18, 2013, IEEE, pp. 1-11.

Notice of Allowance for U.S. Appl. No. 14/482,629, dated Nov. 19, 2015, 8 pages.

Non-Final Office Action for U.S. Appl. No. 14/482,482, dated Jan. 4, 2016, 7 pages.

Notice of Allowance for U.S. Appl. No. 14/482,482, dated Jul. 8, 2016, 8 pages.

Non-Final Office Action for U.S. Appl. No. 14/686,905, dated Apr. 21, 2016, 5 pages.

Notice of Allowance for U.S. Appl. No. 14/686,905, dated Oct. 13, 2016, 7 pages.

Non-Final Office Action for U.S. Appl. No. 15/277,477, dated Nov. 3, 2016, 7 pages.

Notice of Allowance for U.S. Appl. No. 15/277,477, dated Apr. 19, 2017, 9 pages.

\* cited by examiner

FIG. 1

| SeedsList | Seed#1 | Seed#2 | Seed#3 | Seed#4 | BLANK |
|---|---|---|---|---|---|
| $\|Q(t-\Delta)\|$ | 25 | 49 | 102 | 4 | BLANK |
| $\|Q(t)\|$ | 120 | 120 | 135 | 11 | BLANK |
| $\|Q(t+\Delta)\|$ | 155 | 155 | 173 | 44 | BLANK |

FIG. 2A

| SeedsList | Seed#1 | Seed#2 | Seed#3 | Seed#4 | Seed#5 |
|---|---|---|---|---|---|
| $\|Q(t-\Delta)\|$ | 120 | 120 | 135 | 11 | 1 |
| $\|Q(t)\|$ | 155 | 155 | 173 | 44 | 1 |
| $\|Q(t+\Delta)\|$ | 203 | 203 | 244 | 244 | 13 |

| Architecture Requirements Summary ||
|---|---|
| Frame Resolution | 160x120=19200 |
| Memory (Kbytes) | 84 |
| Addition Operations (in Millions) | 10.2776 |
| Product Operations (in Millions) | 0.8206 |
| Memory Read (in Millions) | 34.0631 |
| Memory Write (in Millions) | 33.7197 |
| Estimated Power (μW) | — |

FIG. 10

| PARALLEL MSER DETECTION VS. 2-PASS MSER DETECTION ||||
|---|---|---|---|
| MODE | ADDITION OPERATIONS | PRODUCT OPERATIONS | EXECUTION TIME (S) |
| PARALLEL | 5,206,435 | 448,639 | 4.2009 |
| 2-PASS | 102,775,586 | 820,602 | 8.6742 |

FIG. 11

| PARALLEL MSER DETECTION SAVINGS ||||
|---|---|---|---|
| | ADDITION OPERATIONS | PRODUCT OPERATIONS | EXECUTION TIME (S) |
| | 5,071,151 | 371,963 | 4.4733 |
| % SAVINGS | 49.34 | 45.33 | 51.570 |

FIG. 12

ARCHITECTURE AND METHOD FOR MAXIMALLY STABLE EXTREMAL REGIONS (MSERS)-BASED EXUDATES DETECTION IN FUNDUS IMAGES FOR DIABETIC RETINOPATHY

GOVERNMENT SUPPORT

This invention was made with government funds under contract number 2013-HJ-2440 awarded by ATIC-SRC Center for Energy Efficient Electronic Systems. The U.S. Government may have rights in this invention.

RELATED APPLICATIONS

The present application is related to U.S. Pat. No. 9,489,578, entitled HARDWARE ARCHITECTURE FOR REAL-TIME EXTRACTION OF MAXIMALLY STABLE EXTREMAL REGIONS (MSERs), and U.S. Pat. No. 9,311,555, entitled ARCHITECTURE AND METHOD FOR REAL-TIME PARALLEL DETECTION AND EXTRACTION OF MAXIMALLY STABLE EXTREMAL REGIONS (MSERs).

The present application is related to U.S. Pat. No. 9,600,739, entitled ARCHITECTURE FOR REAL-TIME EXTRACTION OF EXTENDED MAXIMALLY STABLE EXTREMAL REGIONS (X-MSERs), which claims priority to and is a continuation-in-part of U.S. Pat. No. 9,489,578, and which claims priority to and is a continuation-in-part of U.S. Pat. No. 9,311,555.

The present application is related to U.S. patent application Ser. No. 15/277,477, filed Sep. 27, 2016, now U.S. Pat. No. 9,740,947, entitled HARDWARE ARCHITECTURE FOR LINEAR-TIME EXTRACTION OF MAXIMALLY STABLE EXTREMAL REGIONS (MSERs), which claims priority to and is a continuation-in-part of U.S. Pat. No. 9,489,578.

All of the applications listed above are commonly owned and assigned, at the time of the invention, and are hereby incorporated herein by reference in their entireties.

FIELD OF THE DISCLOSURE

The present disclosure relates to computer vision for medical applications.

BACKGROUND

According to the World Health Organization (WHO), the disease diabetes is expected to be the seventh leading cause of death by 2030. In Europe more than 52.8 million people are diagnosed with diabetes, with the number expected to rise to 64 million by 2030. In the United States, a total of 23.6 million people, that is, 7.8% of the U.S. population, have diabetes. However, only 17.9 million of those cases are diagnosed. It was found to be the fourth most frequently managed chronic disease in general practice in 2009, and the projections go as high as the second most frequent disease by the year 2030. Diabetes causes damage to the retina of patients suffering from it for over 10 years. This condition is known as diabetic retinopathy. According to WHO more than 75% of patients who have had diabetes for more than 20 years will develop some form of diabetic retinopathy.

Diabetic retinopathy is a chronic progressive and potentially sight-threatening disease of the retinal microvasculature. It is associated with the diabetes mellitus, which is one of the leading causes of diabetes-related deaths, disabilities, and economic hardship. It is the major cause of visual morbidity due to the presence of clinical abnormalities. Approximately 25,000 people go blind every year because of diabetic retinopathy. Retinal images provide useful information about the status of the eye. The retinal microvasculature is unique in that it is the only part of human circulation that can be directly and non-invasively photographed in vivo.

The presence of exudates in retinal images is one of the primary symptoms of diabetic retinopathy. Consequently, exudate detection has become a significant diagnostic task. To segment exudates, many algorithms require training on clean and filtered reference images, using manual annotation of the individual lesions, which is a tedious and time-consuming task and is prone to human errors.

Further, to optimize automated processing of retina images, the inter- and intra-image variations (e.g., light diffusion and retinal pigmentation) should be taken into account. To eliminate (minimize) such effects, pre-processing is usually required (e.g., contrast enhancement). Moreover, the appearance of exudates shows a rich variety regarding their shapes, locations, and sizes, making automatic detection more challenging.

What is needed is a novel efficient architecture and method to provide an automated detection of exudates in an ocular fundus. The method should be reliably usable to efficiently detect the exudates and be robust against inter-image and intra-image variations while requiring no classifier training associated with machine learning.

SUMMARY

Architecture and a method for maximally stable extremal regions (MSERs)-based detection of exudates in an ocular fundus is disclosed. The architecture includes a communication interface configured to receive pixels of an ocular fundus image. The architecture further includes processing circuitry that is coupled to the communication interface. The processing circuitry is configured to automatically provide labels for light image regions and dark image regions within the ocular fundus image for a given intensity threshold and find extremal regions within the ocular fundus image based on the labels. The maximally stable extremal regions (MSERs) satisfying criteria, further specified in this disclosure, regarding size and intensity indicate the exudates in the ocular fundus. The architecture is further configured to determine MSER ellipses parameters based on the extremal regions and MSER criteria and then to highlight the locations of the exudates in the ocular fundus.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure and, together with the description, serve to explain the principles of the disclosure.

DETAILED DESCRIPTION

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
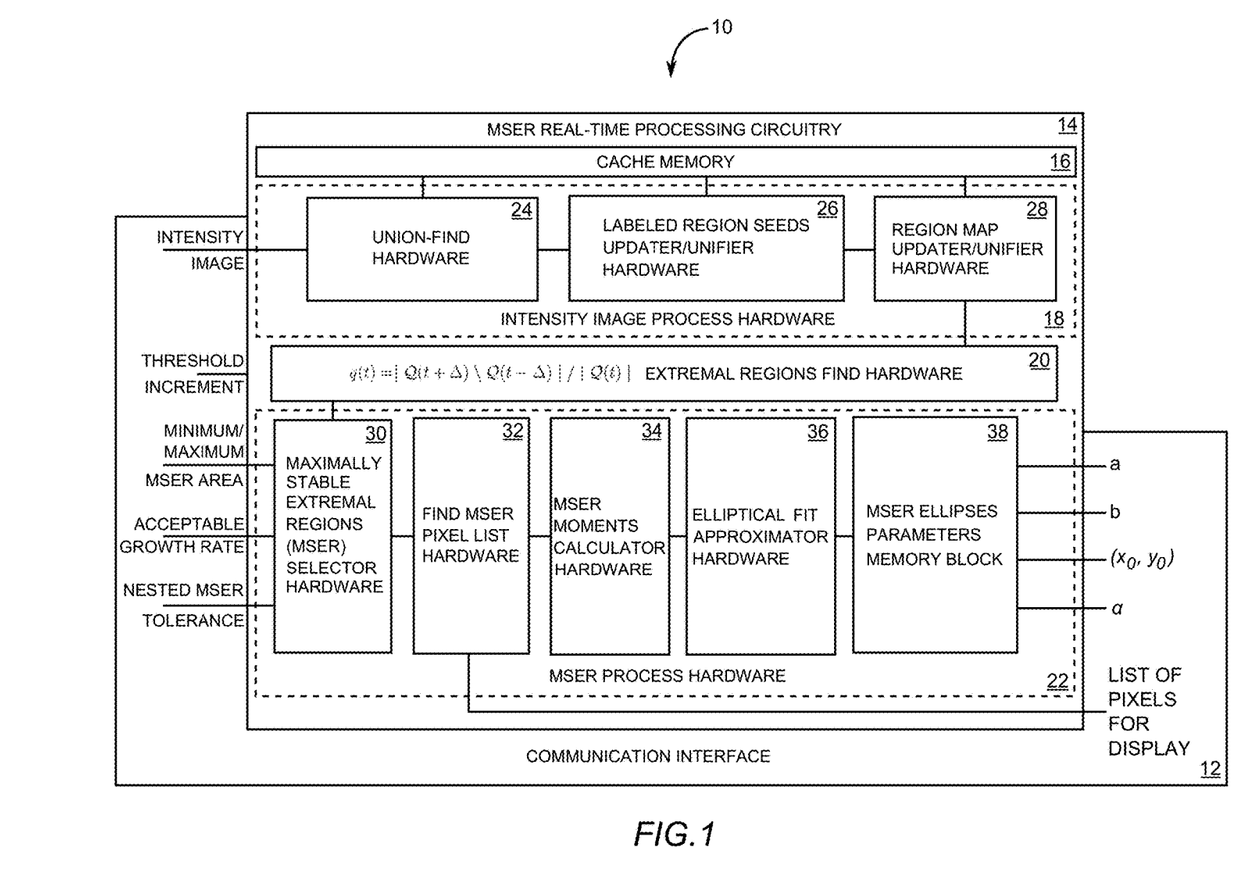
FIG. 1 is a block diagram of the proposed architecture configured for maximally stable extremal regions (MSERs)-based exudates detection of diabetic retinopathy in ocular fundus images in accordance with the present disclosure.

FIG. 1 is a block diagram of an architecture 10 that is configured for maximally stable extremal regions (MSERs)-based exudates detection of diabetic retinopathy in ocular fundus images. The architecture 10 includes a communication interface 12 and MSER real-time processing circuitry 14. In an exemplary embodiment, a cache memory 16 is usable to store data resulting from MSER processing performed by the MSER real-time processing circuitry 14. For the purpose of this disclosure, the architecture combines the required electronic circuits of various hardware implemented functions and memory needed to realize the architecture 10 onto a single integrated chip and as a complete system. An architecture 10 platform can be realized on system-on-chip, a field-programmable gate array, an application-specific integrated circuit, or the like.

The MSER real-time processing circuitry 14 includes intensity image process hardware 18 that receives a data stream of an intensity image that is made up of pixels of an ocular fundus image via the communication interface 12. The MSER real-time processing circuitry 14 provides labels for image regions within the ocular fundus image that match a given intensity threshold. Also included is extremal regions find hardware 20 that finds extremal regions within the ocular fundus image based on the labels. During operation, the extremal regions find hardware 20 automatically monitors the size of each extremal region, that is, each extremal region's cardinality, $|Q(t)|$, as a function of an intensity threshold value t. An MSER is detected if q(t) has a local minimum, where $$q(t)=|\mathcal{Q}(t+\Delta)\backslash \mathcal{Q}(t-\Delta)|/|\mathcal{Q}(t)|. \quad \text{EQ. 1}$$

Detected MSERs are further processed by MSER process hardware 22 to extract MSERs that correlate to pixels within the ocular fundus image that represent exudates. The details of the MSER process hardware 22 are discussed later in this disclosure.

In an exemplary embodiment, an incoming frame of the ocular fundus image is intensity thresholded to generate a binary image made up of dark pixels and bright pixels at full contrast. In an exemplary embodiment, the intensity threshold value t starts at zero and increases at a given intensity threshold increment Δ until the intensity threshold value equals 255. Therefore, if Δ is set to 5, there will be 52 intensity thresholding processes per ocular fundus image frame. Further still, with Δ increments, the threshold continues to increase until the entire ocular fundus image is processed. In general, the thresholding process requires 255/Δ+1 threshold increments. Typical values of Δ range from around about 4 to around about 8. Therefore, around about 64 to around about 8 threshold increments are needed to process a complete ocular fundus image. There is a binary image for each threshold increment, and light regions and dark regions are labeled for each binary image.

In this regard, in an exemplary embodiment, the intensity image process hardware 18 includes union-find hardware 24 that labels image regions within the ocular fundus image for each Δ of the intensity threshold value t. In particular, the union-find hardware 24 labels both light regions made up of the light pixels and dark regions made up of the dark pixels within the binary image for each intensity threshold of the ocular fundus image. The labeling of the light regions and the dark regions occurs during a single pass substantially simultaneously, wherein substantially simultaneously means that the light regions and dark regions are labeled within around about 50% of the overall time needed to run both separately (that is the time needed to run the MSER to detect the bright regions only plus the time needed to run it again to detect the dark regions), based on the present implementation.

Moreover, the union-find hardware 24 provides a labeled image, a seed, and a size (i.e., the number of pixels with a same label) of each region plus the number of labels used. Simply put, the union-find hardware 24 provides labeled regions and their corresponding sizes and seeds. The seed of each region at a particular intensity threshold is the first pixel location that the union-find hardware 24 finds for the region. Due to the intensity threshold increment Δ, previous regions may grow or merge and new regions may appear. As a result, the union-find hardware 24 labels such regions with labels that are still unique but not necessarily similar to previous labels or with the same seeds.

To perform parallel extraction of MSERs, the embodiments of this disclosure monitor both dark regions and white regions substantially simultaneously. However, each labeled region has a unique label regardless of whether or not the region is a dark region or a light region. In order to label dark regions and light regions substantially simultaneously, the union-find hardware 24 is configured first to define two matrices of M×N size in order to hold a binary image resulting from thresholding. A first matrix referred to herein as the $\mathfrak{FD}$ matrix, is represented as follows:

$$\mathfrak{FD} = \begin{bmatrix} 1 & M+1 & \cdots & M(N-1) \\ 2 & M+2 & \ddots & M(N-1)+1 \\ \vdots & \vdots & \ddots & \vdots \\ M & 2M & \cdots & MN \end{bmatrix}_{M \times N} \quad \text{EQ. 2}$$

which effectively assigns unique labels to all pixels regardless of pixel color, that is, black or white. In particular, all pixels are singletons initially with label values ranging from 1 to M×N.

A second matrix defines the size of each region, and since initially all pixels are considered singletons, a region size matrix, referred to herein as the $\mathfrak{Rs}$ matrix is represented as follows:

$$\mathfrak{Rs} = \begin{bmatrix} 1 & \cdots & 1 \\ \vdots & \ddots & \vdots \\ 1 & \cdots & 1 \end{bmatrix}_{M \times N} \quad \text{EQ. 3}$$

The values stored in the $\mathfrak{FD}$ and $\mathfrak{Rs}$ matrices are updated as the union-find hardware 24 scans for connectivity between pixels. For example, the union-find hardware 24 can scan for eight-pixel connectivity or four-pixel connectivity.

Furthermore, because the regions can grow and/or merge, the first pixel location that the union-find hardware 24 encounters for a growing region is different from a previous seed, even though both refer to the same region. To overcome this problematic issue, labeled region seeds updater/unifier hardware 26 compares all seeds stored as a seed list in the cache memory 16 for a present intensity threshold to seeds previously detected and stored in the seed list. If a match between seeds is found, the original seed is maintained by the labeled region seeds updater/unifier hardware 26. Otherwise, the labeled region seeds updater/unifier hardware 26 appends a new seed to the seeds list stored in the cache memory 16.

In an exemplary embodiment, for both light pixels and dark pixels, if a pixel P with a seed r has the same intensity as a pixel below and to its right, the seed of the pixel below and to its right, the $\mathfrak{FD}$ matrix, is changed to r P, and the corresponding value in the $\mathfrak{Rs}$ matrix changes to the count value of the pixels with the seed label. At the end of this process, the $\mathfrak{FD}$ matrix is labeled by the region root. That is to say, the root of a specific region becomes the region's label. Similarly, the $\mathfrak{Rs}$ matrix is identified by a region size instead of the root value. Note that the $\mathfrak{FD}$ labels are unique, whereas the $\mathfrak{Rs}$ labels are not. In particular, two different regions can have the same region size, however, each has only one root.

A region map is usable to store region sizes for the seeds in the seeds list. The region map is stored as a dedicated portion of the cache memory 16. Region map updater/unifier hardware 28 updates the region map as the ocular fundus image is processed by the union-find hardware 24.

Figure 2A:
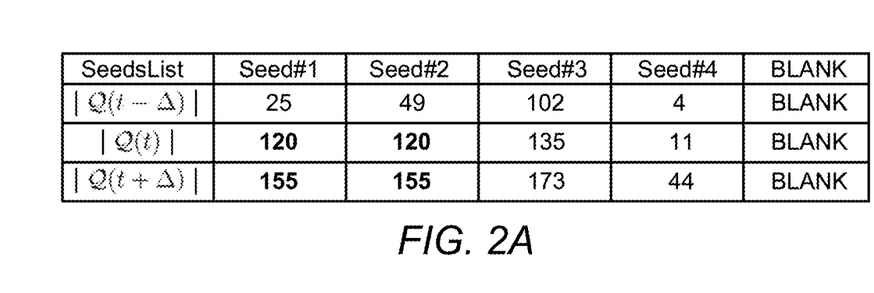
FIG. 2A is a sample scenario table for a seed list at a third intensity threshold MSERs extraction.
Figure 2B:
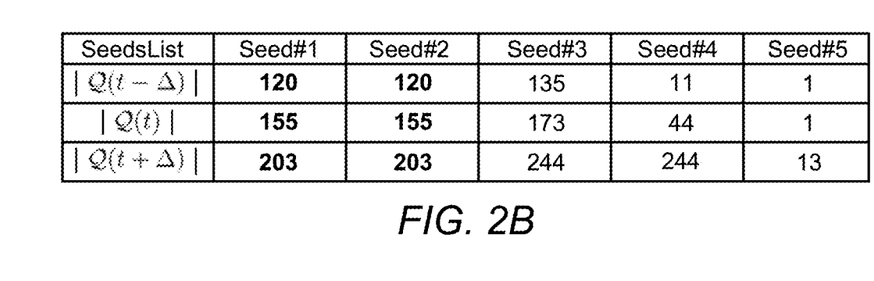
FIG. 2B is an updated sample scenario table for the seed list at a fourth intensity threshold MSERs extraction.

The amount of memory that is needed to store the seeds' region sizes is 3 times the number of seeds stored in the SeedList memory because the region map stores the value of $\mathcal{Q}(t+\Delta)$, $\mathcal{Q}(t)$, and $\mathcal{Q}(t-\Delta)$ for each seed. These values are needed to calculate the stability function for each seed in the SeedList. The region map allows for memory reduction and efficiency in place of recording the region size for every seed in the SeedList at every intensity threshold. As a result, if more seeds are appended to the SeedList at intensity threshold t+Δ, then new locations for this new seed are also appended to the RegionMap, where the region size for this intensity threshold is added in the q(t)=|Ω(t+Δ)|, while |Ω(t)| and |Ω(t−Δ)| are filled with ones to avoid division by zero. Note, that since |Ω(t+Δ)| is not available at the current intensity threshold t, nor is t available for the first intensity threshold, then the calculation of q(t) starts at the third intensity threshold, that is, q(t) is calculated at intensity threshold t+Δ, excluding the first and final intensity threshold values. In this way, the RegionMap memory has three rows to allow the stability function to be easily calculated. To elaborate on this, consider the following sample scenario table shown in FIG. 2A. At the third intensity threshold, in FIG. 2A, q(t) is calculated for the second intensity threshold. At |Ω(t)|, the two regions defined by Seed#1 and Seed#2 merge, so they have the same size from then on. At the fourth intensity threshold, in FIG. 2B, q(t) is calculated for the third intensity threshold, and note that |Ω(t+Δ)| and |Ω(t)| at the third intensity threshold are |Ω(t)| and |Ω(t−Δ)| at the fourth intensity threshold. Because of the detection of a new region, defined by Seed#5, the RegionMap list is appended and the size of this new region at |Ω(t+Δ)| is filled with its size, while |Ω(t)| and |Ω(t−Δ)| are filled with ones. At this intensity threshold, regions referred to by Seed#3 and Seed#4 merge so they will have the same region size from now on, etc. Note that at the final intensity threshold, all regions merge into one with a size M×N.

The communication interface 12 receives MSER criteria that in at least one embodiment includes a minimum MSER area value MinArea, a maximum MSER area value MaxArea, and an acceptable growth rate value MaxGrowth. The minimum MSER area is the minimum number of pixels that an MSER can contain. In contrast, the maximum MSER area is the maximum number of pixels that an MSER can contain. As such, all detected MSERs must satisfy the condition:

$$\text{MinArea} \leq \Omega \leq \text{MaxArea}. \qquad \text{EQ. 4}$$

The communication interface 12 passes the MSER criteria to MSER selector hardware 30, which also receives MSERs found via the extremal regions find hardware 20. The MSER selector hardware 30 in turn tests each MSER to ensure that each MSER has an area that fits within the range specified by the minimum MSER area value MinArea and the maximum MSER area value MaxArea.

The maximum acceptable growth rate value MaxGrowth specifies how stable the detected MSERs must be. In particular, all detected MSERs must satisfy the condition:

$$q(t)=|\Omega(t+\Delta)\backslash\Omega(t-\Delta)|/|\Omega(t)|\leq \text{MaxGrowth}. \qquad \text{EQ. 5}$$

The communication interface 12 passes maximum acceptable growth rate value MaxGrowth to the MSER selector hardware 30, which in turn tests each MSER found by the extremal regions find hardware 20 to ensure that each MSER does not exceed the maximum acceptable growth rate value MaxGrowth.

In one embodiment, the MSER criteria also include a nested MSER tolerance value τ that is provided to mitigate sensitivity to blur and to mitigate discretization effects that plague traditional MSER extraction software and/or hardware. Since nested MSERs have similar center coordinates, any new MSERs with centers within a range associated with the tolerance value τ compared with previously detected and stored MSERs are excluded automatically. In particular, all detected MSERs satisfy the following conditions:

$$x_0 : \notin \{(1-0.5\tau)x_i,(1+0.5\tau)x_i\}, \qquad \text{EQ. 6}$$

$$y_0 : \notin \{(1-0.5\tau)y_i,(1+0.5\tau)y_i\}, \qquad \text{EQ. 7}$$

where $x_i$ and $y_i$ denote all previously stored center values of the detected MSERs. However, comparing centers has a drawback in that unnecessary computations are included while image moments are calculated. To predict possible nesting and hence save unnecessary operations due to comparing centers, an alternative approach is executed by the MSER selector hardware 30 at a relatively far lower computational cost. Specifically, for each region, the MSER selector hardware 30 compares a current growth rate with a previous growth rate, and if an absolute difference is within a range defined by the tolerance value τ, then this region at the current intensity threshold is excluded by the MSER selector hardware from further MSER extraction processing. Moreover, an exemplary intensity threshold increment, Δ, may be selected as 5 to speed up the MSER detection process. MSER detection with Δ equal to 5 is around about five times faster than when Δ is equal to 1. Further still, since merged regions have the same growth rate from the intensity threshold level as they merge, only one MSER that corresponds to the region with a seed that comes first in the seed list is detected. The remaining MSERs are not processed but instead are ignored. As a result of ignoring the remaining MSERs, many other unnecessary computations are eliminated to further save energy and execution time.

Find MSER pixel list hardware 32 generates a pixel list for the x and y coordinates for each labeled region defined by the labeled regions seed stored in the seed list for every MSER that passes the conditions tested by the MSER selector hardware 30. The find MSER pixel list hardware 32 outputs an MSER pixel list, which is a list of pixels for display, through the communication interface 12 to display hardware that displays ocular fundus images. Pixels within the list of pixels for display represent exudates and are highlighted by the display hardware by a change in characteristic such as color or contrast. In at least one embodiment, pixels within the list of pixels are highlighted and displayed by the display hardware with a red, green, blue color value change. In an exemplary embodiment, pixels within the pixel list for display have their color value increased to a maximum red, green, blue color level value of 255.

Alternatively or cumulatively, MSER moments calculator hardware 34 uses the pixel list to calculate region moments using the following relationship for any particular moment $m_{pq}$:

$$m_{pq}=\Sigma_{(x,y)\in R}x^p y^q, \qquad \text{EQ. 8}$$

$$x,y\in R(\tau) \qquad \text{EQ. 9}$$

where x and y denote the pixel coordinate of the region R(τ) at the current intensity threshold. Subsequently, the region can be approximated by a best-fit ellipse equation that is given by the following equation:

$$\frac{(x-x_0+\tan(\alpha)(y-y_0))^2}{a^2(1+\tan^2(\alpha))}+\frac{(y-y_0+\tan(\alpha)(x-x_0))^2}{b^2(1+\tan^2(\alpha))}=1, \qquad \text{EQ. 10}$$

where $(x_0, y_0)$, a, b, and α, respectively, are MSER ellipse parameters that represent a center of gravity (center of the MSER ellipse), a major axis length, a minor axis length, and an angle of the major axis with respect to a horizontal axis. In an exemplary embodiment, the MSER ellipse parameters are determinable using region moments $m_{00}$, $m_{10}$, $m_{10}$, $m_{11}$, $m_{02}$, and $m_{20}$ that are calculated by MSER moments calculator hardware 34. Elliptical fit approximator hardware 36 uses the region moments provided by the MSER moments calculator hardware 34 to approximate the MSER ellipse parameters ($x_0$, $y_0$), a, b, and α via the following mathematical relationships.

$$x_0 = \frac{m_{10}}{m_{00}},\qquad \text{EQ. 11}$$

$$y_0 = \frac{m_{01}}{m_{00}},\qquad \text{EQ. 12}$$

$$a = \sqrt{2\left(t_1 + t_3 + \sqrt{t_2^2 + (t_3 - t_1)^2}\right)},\qquad \text{EQ. 13}$$

$$b = \sqrt{2\left(t_1 + t_3 - \sqrt{t_2^2 + (t_3 - t_1)^2}\right)},\qquad \text{EQ. 14}$$

$$\alpha = 0.5\ \tan^{-1}\left(\frac{t_2}{t_1 - t_3}\right),\qquad \text{EQ. 15}$$

where $$t_1 = \frac{m_{20}}{m_{00}} - x_0^2,\qquad \text{EQ. 16}$$

$$t_2 = 2\left(\frac{m_{11}}{m_{00}} - x_0 y_0\right),\qquad \text{EQ. 17}$$

$$t_3 = \frac{m_{02}}{m_{00}} - y_0^2,\qquad \text{EQ. 18}$$

Instead of storing each MSER pixels list, which would require a relatively huge memory, an MSER ellipses parameters memory block 38 is usable to store best-fit ellipses parameters ($x_0$, $y_0$), a, b, and α, which are provided to external hardware (not shown) for display or monitoring. For example, since the best-fit ellipses parameters ($x_0$, $y_0$), a, b, and α are readily available through the communication interface 12, they can be used to compute scale invariant feature transform descriptors and speeded up robust features descriptors. Depending on whether or not the ocular fundus image is inverted, the architecture 10 detects and extracts either bright or dark MSERs.

Figure 3A:
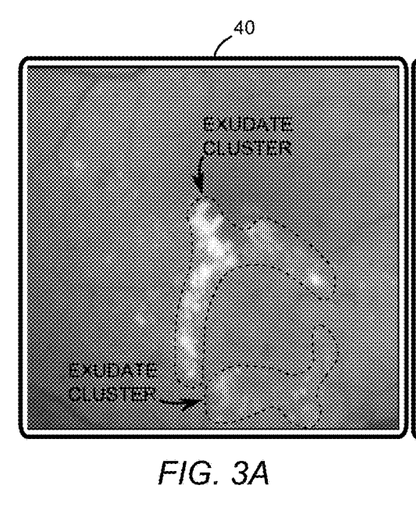
FIG. 3A is a raw image of an ocular fundus having exudates that are a primary symptom of diabetic retinopathy.

FIG. 3A is a raw image of an ocular fundus having exudates that are a primary symptom of diabetic retinopathy. Regions shown within the raw image in dashed line are two exudate clusters. Relatively sporadic exudates occur outside the two exudate clusters. Embodiments of the present disclosure also locate and highlight these exudates.

In one embodiment, the raw ocular fundus image comes from a green channel of a red, green, blue image. However, other color channels such as cyan, magenta, yellow, and black (CMYK) from a CMYK image are also usable as intensity images in some embodiments. In yet other embodiments, grayscale images are usable as intensity images. In some embodiments, the intensity between bright and dark regions has 255 levels of intensity. However, it is to be understood that levels of intensity ranging between 127 and 1024 are also usable for detection of exudates using other embodiments of the present disclosure.

Figure 3B:
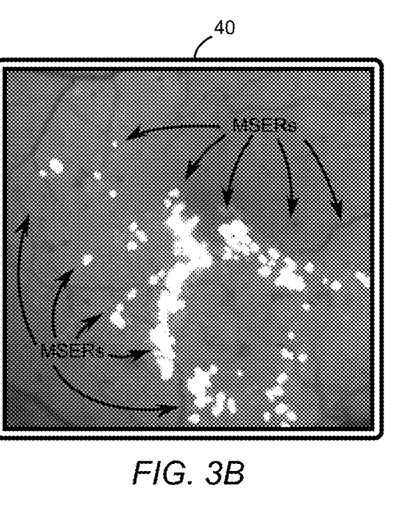
FIG. 3B is a processed ocular fundus image displaying MSERs representing detected and extracted exudates from the raw ocular fundus image of FIG. 3A.

FIG. 3B is an ocular fundus image processed by an exemplary embodiment of the present disclosure. The processed ocular fundus image of the ocular fundus image displays ellipses for MSERs representing detected and extracted exudates from the raw ocular fundus image of FIG. 3A. Notice that the exudates outside the exudate clusters are also located and highlighted by the exemplary embodiment.

Moreover, accuracy and sensitivity in locating the exudates within and outside the exudate clusters is achieved without any preprocessing of the raw ocular fundus image of FIG. 3A. The ability to locate and highlight exudates without external preprocessing is a benefit of embodiments of the present disclosure.

Figure 3C:
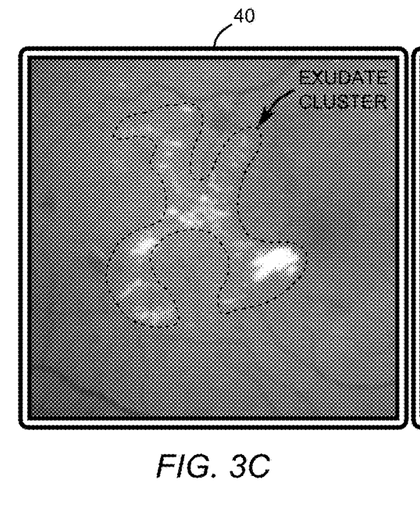
FIG. 3C is another raw image of an ocular fundus having exudates that are a primary symptom of diabetic retinopathy.
Figure 3D:
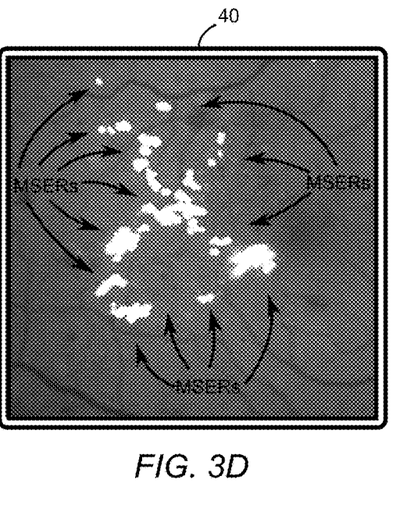
FIG. 3D is a processed ocular fundus image displaying MSERs representing detected and extracted exudates from the raw ocular fundus image of FIG. 3C.

FIG. 3C is another raw image of an ocular fundus having exudates that are a primary symptom of diabetic retinopathy. This exemplary image contains a particularly bright exudate within a lower right branch of an exudate cluster indicated in the raw image. While related art techniques have difficulty resolving between exudates with large contrasts, embodiments of the present disclosure have a relatively high dynamical range of detection of exudates as evidenced in the following MSER processed image of FIG. 3D. In an exemplary embodiment, MSER processed images are displayed on a display hardware 40 that is in communication with the communication interface 12 (FIG. 1). The display hardware 40 is an electronic display such as a liquid crystal display (LCD).

In general, a minimum size in pixels for a bright MSER representing an exudate is given by the following equation:

$$\text{Minimum size} = 0.00006 * (\text{eye diameter in pixels})^2 \qquad \text{EQ. 19}$$

For example, a minimum size for a bright MSER representing an exudate for an eye diameter of an ocular fundus image of 2000 pixels is 240 pixels.

Also, in general, a maximum sized major axis in pixels for a bright MSER representing an exudate is given by the following equation:

$$\text{Maximum size} = 0.00018 * (\text{eye diameter in pixels})^2 \qquad \text{EQ. 20}$$

For example, a maximum size for a bright MSER representing an exudate for an eye diameter of an ocular fundus image of 2000 pixels is 7200 pixels.

Figure 4:
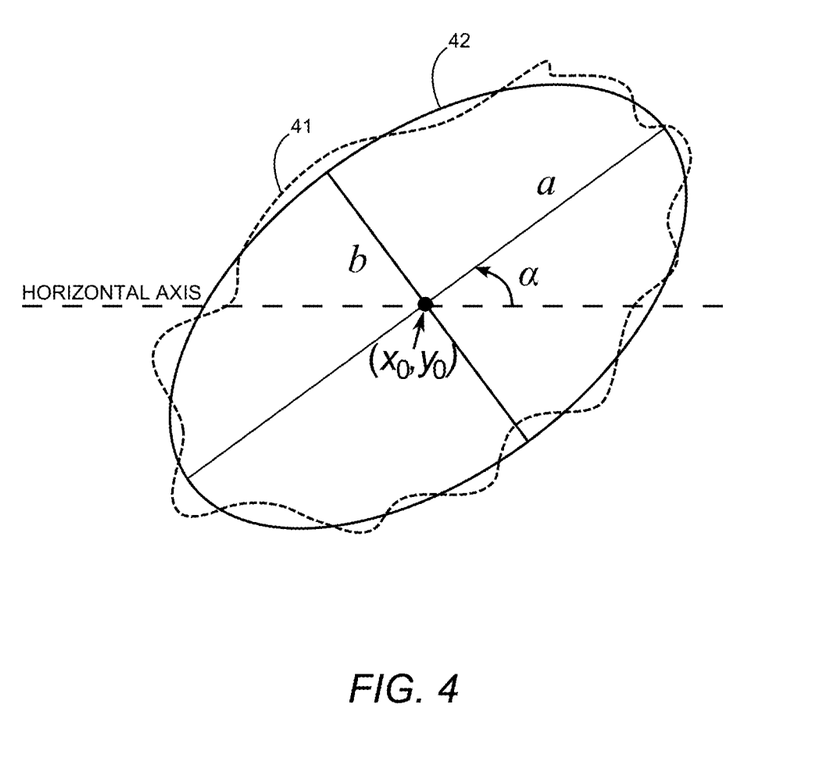
FIG. 4 is an exemplary contour sketch of an irregularly shaped MSER with a best-fit elliptical approximation.

FIG. 4 is an exemplary contour sketch of an irregularly shaped MSER 41 with a best-fit elliptical approximation 42. Note that in exudate detection, best-fit elliptical approximations play only a supplementary role in some embodiments and an optional role other embodiments and no role in yet other embodiments.

Figure 5:
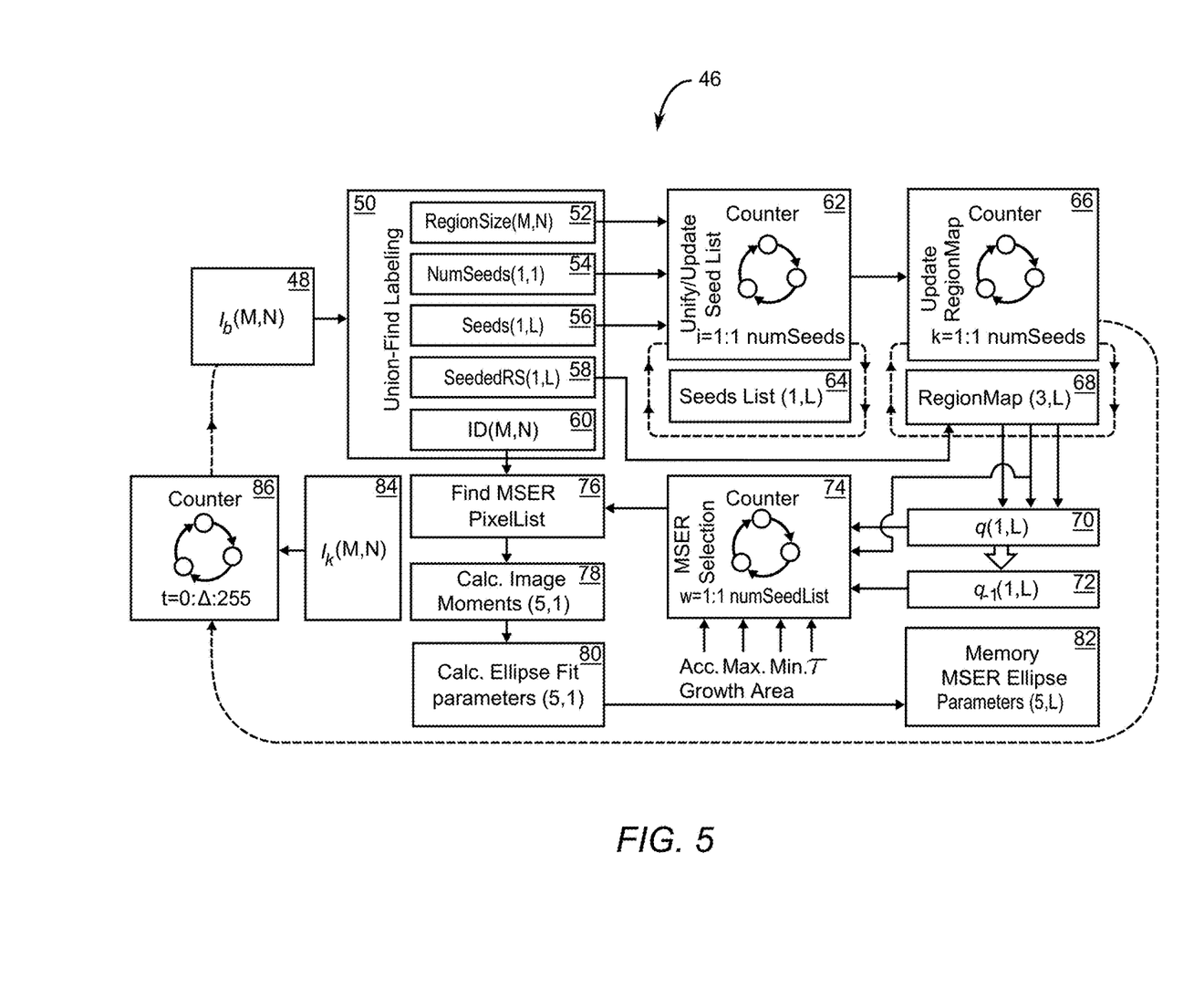
FIG. 5 is a diagram for a process flow for the MSERs processing hardware of FIG. 1.

FIG. 5 is a diagram for a process flow 46 for the MSER real-time processing circuitry 14 (FIG. 1). Note that dashed lines represent loop operations. The MSER real-time processing circuitry 14 reserves a memory block 48 having M rows and N columns to store an M×N binary (i.e., intensity threshold) image derived for the ocular fundus image. A union-find labeling process 50 generates a region size array 52, a number of seeds variable 54, a list of seeds 56, a seeded region size list 58 that includes the seed and the size (i.e., the number of pixels with the same label) of each region, and a labeled image array 60.

The labeled region seeds updater/unifier hardware 26 (FIG. 1) implements a finite state machine (FSM) 62 that monitors the labels of regions to relate them according to their previous label values in order to maintain tracking of the same region's seeds and sizes to ensure proper MSER detection. If the current intensity threshold includes a region that has a different seed from the previous intensity threshold value, the previous seed is maintained; otherwise, a new seed is appended to a seed list 64 by FSM 62.

The region map updater/unifier hardware 28 (FIG. 1) implements an update region map FSM 66 that is labeled in FIG. 5 as Update RegionMap. After unifying and updating the seed list 64, the FSM 66 maps the number of pixels in a region of each monitored region having a seed stored in the seed list 64. The mapping performed by the FSM 66 results in a region map array 68 that is, in this exemplary embodiment, named RegionMap (3, L). The region map array 68 is a 3×L array stored in cache memory 16 (FIG. 1).

In this exemplary embodiment, the region map array 68 stores the region size of each region having a seed in the seed list 64 for the current intensity threshold value and the previous two intensity threshold values. This is sufficient to calculate the growth rate or stability function of each region that is used to identify MSERs. Note that the stability function is defined as follows:

$$q(t)=|\mathcal{Q}(t+\Delta)\setminus\mathcal{Q}(t-\Delta)|/|\mathcal{Q}(t)| \qquad \text{EQ. 21}$$

and $\mathcal{Q}(t+\Delta)$, $\mathcal{Q}(t)$, and $\mathcal{Q}(t-\Delta)$ are stored for every seeded region in the region map array 68. A q(t) memory array 70 is usable to store the results of the stability function at the current intensity threshold. A q(t−Δ) memory array 72 is usable to store the results of the stability function at the current intensity threshold minus Δ.

The MSER selector hardware 30 (FIG. 1) implements an MSER selection FSM 74 that performs selection of MSERs based on the values stored in the q(t) memory array 70 and q(t−Δ) memory array 72, along with MSER criteria received via the communications interface 12 (FIG. 1). The MSER criteria pertaining to the minimum MSER area value MinArea and the maximum MSER area value MaxArea are used by the MSER selection FSM 74 to exclude relatively too small MSERs and to exclude relatively too large MSERs. All MSERs $\mathcal{Q}$ detected by the MSER selection FSM 74 satisfy the following relationship:

$$\text{MinArea} \leq \mathcal{Q} \leq \text{MaxArea} \qquad \text{EQ. 22}$$

The MSER selection FSM 74 uses the third parameter that pertains to the maximum acceptable growth rate value MaxGrowth to monitor the stability of the detected MSERs, which must satisfy the following relationship:

$$q(t)=|\mathcal{Q}(t+\Delta)\setminus\mathcal{Q}(t-\Delta)|/|\mathcal{Q}(t)| \leq \text{AccGrth} \qquad \text{EQ. 23}$$

Moreover, the MSER selection FSM 74 compares the growth rate of q(t) and q(t−1). If the comparison does not exceed the nested MSER tolerance value τ, then a nested MSER is detected and the MSER selection FSM 74 does not detect that particular nested MSER again.

The find MSER pixel list hardware 32 (FIG. 1) implements a find MSER pixel list function 76 that scans the binary image to locate all pixels belonging to each MSER detected. Afterwards, the MSER moments calculator hardware 34 (FIG. 1) implements a calculate image moments function 78 that calculates the region moments $m_{00}$, $m_{10}$, $m_{10}$, $m_{11}$, $m_{02}$, and $m_{20}$ that are stored in a 5×1 memory array stored in the cache memory 16 (FIG. 1). Next, the elliptical fit approximation hardware 36 (FIG. 1) implements a calculate ellipse fit parameters function 80 that calculates the best-fit ellipses parameters ($x_0$, $y_0$), a, b, and α, which are stored in the MSER ellipses parameters memory block 38 (FIG. 1) via a memory MSER parameters store parameters function 82. The MSER parameters are stored using a 5×L memory array.

An ocular fundus image store function implemented by the MSER real-time processing circuitry 14 (FIG. 1) allocates a memory array $I_k(M,N)$ 84 within the cache memory 16. The MSER real-time processing circuitry 14 also implements an FSM 86 that uses values from the memory array $I_k(M,N)$ to perform an intensity thresholding of the ocular fundus image at every intensity threshold increment Δ.

Figure 6:
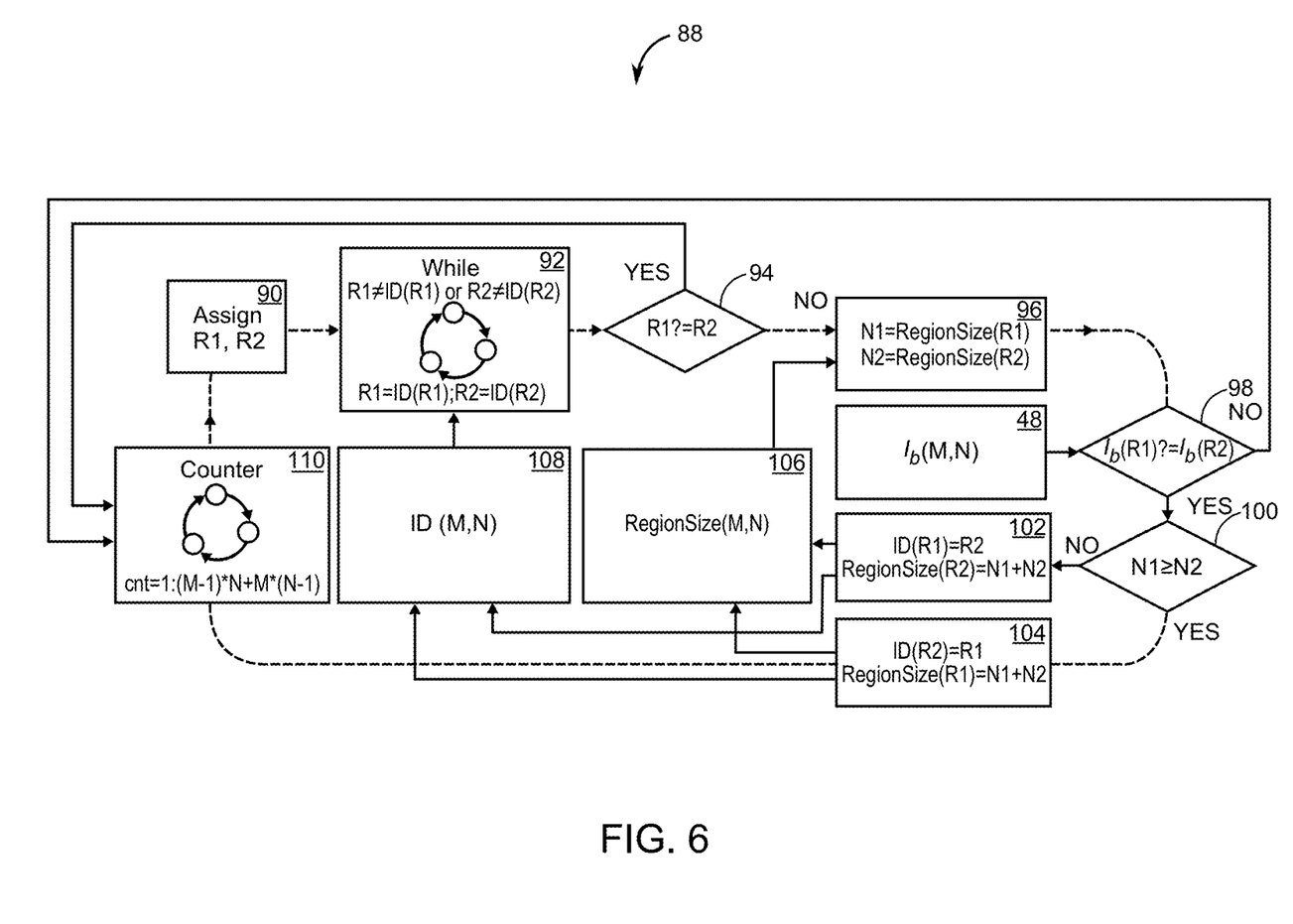
FIG. 6 is a diagram for a process flow for the union-find processing hardware of FIG. 1.

FIG. 6 is a process flow 88 for the union-find hardware 24 (FIG. 1). Note dashed lines represent loop operations. In particular, the union-find hardware 24 implements an assign function 90 that assigns two relatively well-defined values for a pair of region roots (R1, R2) needed for the union-find labeling in accordance with the present disclosure. Note that the region roots (R1, R2) address two adjacent pixel identification (ID) memory addresses.

A first union-find FSM 92 compares the assigned region roots (R1, R2) to stored values at ID memory addresses. The first union-find FSM 92 makes the region roots (R1, R2) the same if the first union-find FSM 92 determines that the region roots (R1, R2) are different. As the first union-find FSM 92 operates, yet another comparison is made by a first decision diamond 94 to test if the region roots (R1, R2) are the same. If no, the process continues with an assignment function 96 that assigns two variables (N1, N2) with two values respectively, with the stored values at the ID memory addresses for region roots (R1, R2) that correspond to the region size of a collective region defined by the region roots (R1, R2).

A second decision diamond 98 compares two adjacent pixels specified by the region roots (R1, R2) to determine if the two adjacent pixels have the same value. If no, then there is no change. However, if yes, then the two adjacent pixels are connected and the process continues to a third decision diamond 100 that tests to see if N1 is greater than or equal to N2. If no, the process continues with a first merge block 102 that merges N1 and N2 into the region R2, which is relatively larger than region R1. If yes, the process continues with a second merge block 104 that merges N1 and N2 into the region R1. The first merge block 102 and the second merge block 104 communicate with a region size memory array 106 that has M×N elements and is named RegionSize (M, N) in the exemplary embodiment of FIG. 6. A uniquely labeled image is stored within an ID matrix 108. Unlike the region size memory array 106 that is labeled using each region number of pixels in which two regions might coincidentally have the same region size and hence the same label in the ID matrix 108, labels in the ID matrix 108 are unique, and each label reflects the root of the associated region. In other words, since each region has just one root, each label is unique.

A region roots assignment FSM 110 continues assigning values for the region roots (R1, R2) and continues operating for every intensity threshold until all pixels are labeled. Each root (i.e., each of R1 and R2) is assigned M*(N−1)+N*(M−1) times.

A total memory requirement for a frame of M×N and a maximum number of L detected MSERs can be approximated as follows:

Total Memory Requirement≈M×N[ocular fundus image]+0.125×M×N[binary image,one bit per location is sufficient]+2×k×M×N[ID+RegionSize]+4×L[Seeds List+RegionMap]+5×L[elliptical parameters]+2×L[q(t) and q(t−1]=[1.125+2× k]×M×N+11×L, where k is a constant that ensures proper assignment for both RegionSize and ID, not larger than 3 to support 4096×4096 image resolution, which is, again, far more than needed in practice.

Figure 7:
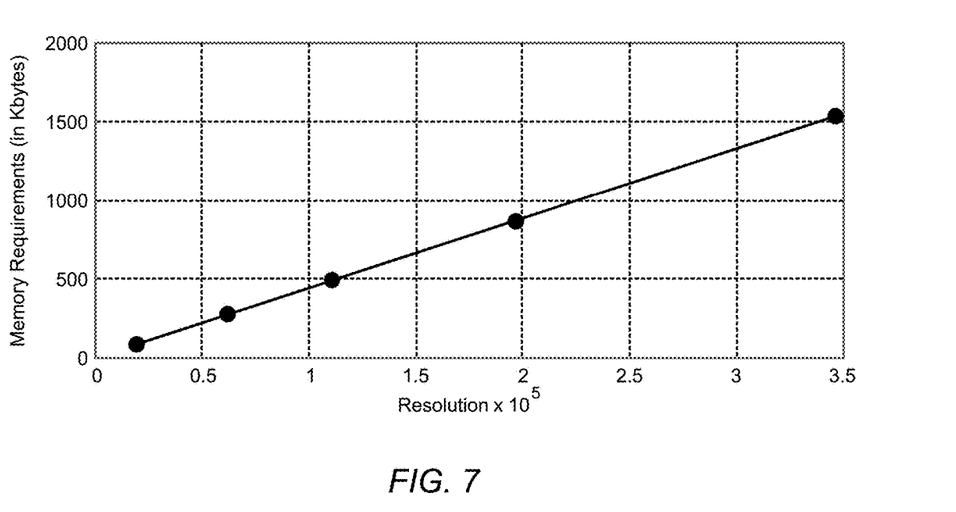
FIG. 7 is a graph of memory requirements of the architecture versus ocular fundus image resolution.

The total memory requirement is an upper limit approximation that is recommended because of the impossibility to predict the number of MSERs in an image, since the number of MSERs depends highly on the content of the image. The memory requirement is only about 104 kilobytes (kB) for a 160×120 frame (and assuming the constant k=2), and a maximum of 768 detected MSERs, which is relatively far more than the typical number of detected MSERs in images. If one assumes an image resolution of 320×240, just as used in a state-of-art field-programmable gate array implementation, then the memory requirement tends to be around about 393 kB, which is about 91.6% less than the reported memory requirement of 4.6 megabytes in use in typical related art applications. A sample plot for different resolutions, namely 160×120, 288×216, 384×288, 512×384, and 682×512, is shown in FIG. 7, which shows a linear trend for memory versus image size (assuming k=1).

The architecture 10 of FIG. 1 does not perform complex image operations such as filtering, smoothing, Fourier transform, etc. In particular, only addition and multiplication are used during processing of one embodiment of the architecture 10. The bulk of these operations mainly come from image moments calculations to find the five best-fit ellipses parameters ($x_0$, $y_0$), a, b, and α of the elliptical fit approximation, plus the union-find labeling process 50 (FIG. 5). The remainder of the operations are mainly assignment and comparison such as those executed during an intensity thresholding of the ocular fundus image into binary image.

Figure 8:
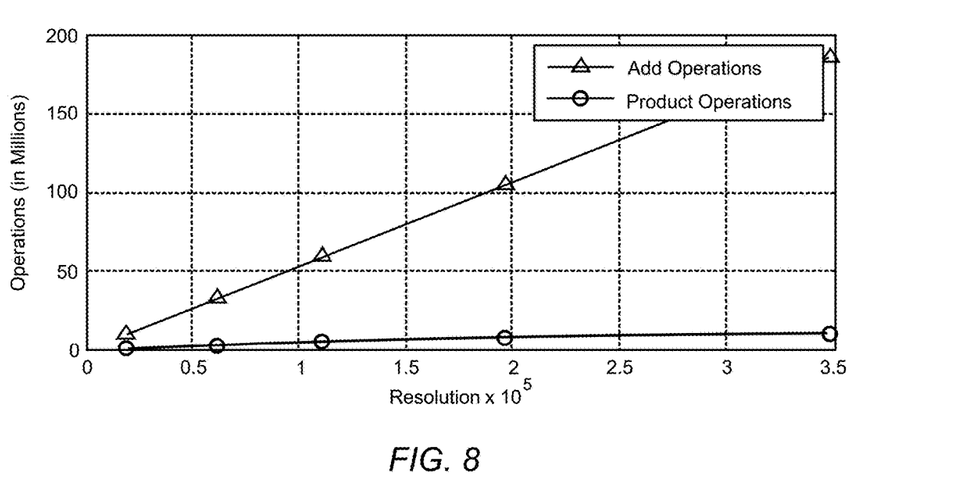
FIG. 8 is a graph of add and product operations for the architecture versus ocular fundus image resolution.
Figure 9:
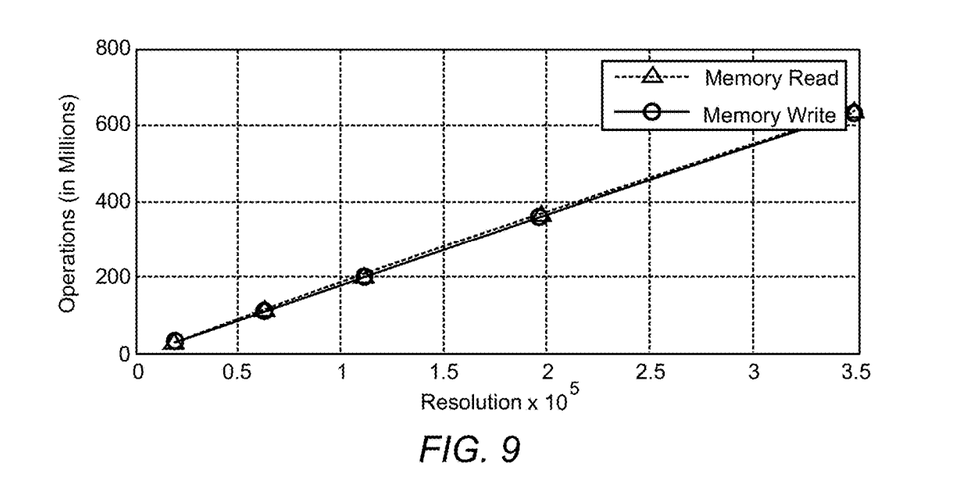
FIG. 9 is a graph of memory read and write operations for the architecture versus ocular fundus image resolution.
Figure 10:
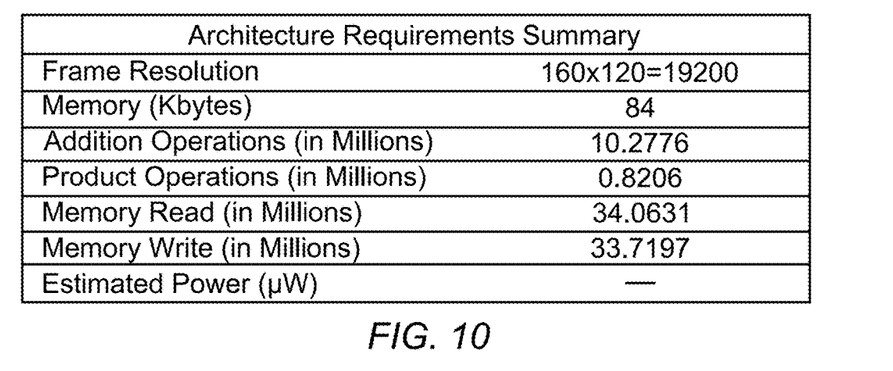
FIG. 10 is a first table providing an architecture requirements summary.
Figure 11:
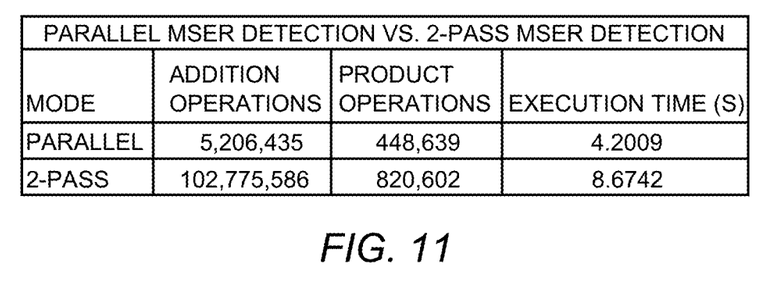
FIG. 11 is a second table that compares the parallel MSER detection and extraction of the present disclosure with two-pass MSER detection and extraction.
Figure 12:
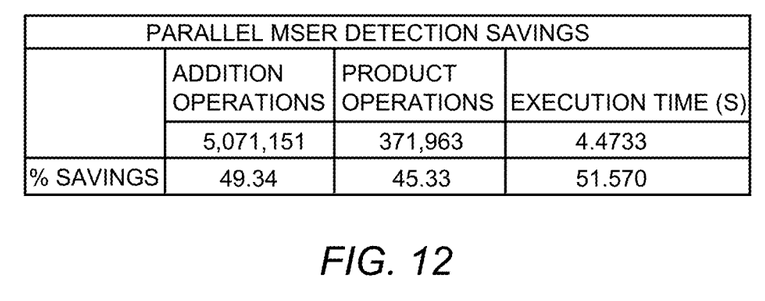
FIG. 12 is a third table that presents parallel MSER detection and extraction savings in both absolute values and percentage values.

In particular, FIG. 8 is a plot of add operations and product operations versus resolution, whereas FIG. 9 is a plot of memory read and memory write operations versus resolution. A test image at different resolutions 160×120, 288×216, 384×288, 512×384, and 682×512 was used to generate the plots shown in FIG. 8 and FIG. 9. FIG. 10 is a table that summarizes the architectural requirements of an exemplary embodiment of architecture 10 (FIG. 1). The exemplary requirements summary was produced using the same test image to generate FIGS. 7, 8, and 9. FIG. 11 is a second table that compares this disclosure's parallel MSER detection and extraction with two pass MSER detection and extraction. FIG. 12 is a third table that presents parallel MSER detection and extraction savings in both absolute values and percentage values.

Those skilled in the art will recognize improvements and modifications to the embodiments of the present disclosure. All such improvements and modifications are considered within the scope of the concepts disclosed herein and the claims that follow.

What is claimed is:

1. Architecture for maximally stable extremal regions (MSERs)-based detection of exudates in an ocular fundus comprising:
   a communication interface configured to receive pixels of an ocular fundus image; and
   processing circuitry having a memory coupled to the communication interface, wherein the processing circuitry is configured to automatically:
   store the pixels of the ocular fundus image within the memory;
   provide labels within the memory for light image regions and dark image regions within the ocular fundus image for a given intensity threshold;
   find MSERs within the stored pixels of the ocular fundus image based upon the labels;
   generate an MSER pixel list based on the MSERs and MSER criteria that include a minimum MSER size in pixels and a maximum MSER size in pixels based upon an eye diameter size in the stored pixels of the ocular fundus image and store the MSER pixel list within the memory; and
   provide for display through the communication interface the pixels of the ocular fundus image that are located within the MSER pixel list to indicate the exudates in the ocular fundus.

2. The architecture of claim 1 wherein the processing circuitry is configured to substantially simultaneously provide the labels for the light image regions and the dark image regions within the ocular fundus image for the given intensity threshold.

3. The architecture of claim 1 wherein the processing circuitry is configured to provide the labels for the light image regions and the dark image regions within the ocular fundus image during a single processing pass for the given intensity threshold.

4. The architecture of claim 1 wherein the MSER criteria include a nested MSER tolerance value.

5. The architecture of claim 4 wherein the MSER criteria further include a minimum MSER area, a maximum MSER area, and an acceptable growth rate value for MSER areas.

6. The architecture of claim 1 wherein the processing circuitry is further configured to determine MSER ellipses parameters that include a center of gravity, a major axis length, a minor axis length, and an angle of the major axis length with respect to a horizontal axis.

7. The architecture of claim 1 wherein the processing circuitry includes MSER moments calculator hardware configured to calculate MSER moments.

8. The architecture of claim 7 wherein the processing circuitry further includes elliptical fit approximator hardware configured to receive the MSER moments from the MSER moments calculator hardware and fit an MSER ellipse to an extremal region based upon the MSER moments.

9. The architecture of claim 1 wherein the processing circuitry includes union-find hardware configured to provide the labels for the light image regions and the dark image regions within the ocular fundus image for the given intensity threshold t.

10. The architecture of claim 9 wherein the processing circuitry includes extremal region find hardware that is configured to receive the labels for the light image regions and the dark image regions and find extremal regions based upon the labels for the light image regions and the dark image regions.

11. The architecture of claim 10 wherein the extremal region find hardware is configured to find extremal regions using a mathematical relationship $q(t)=|Q(t+\Delta)\backslash Q(t-\Delta)|\backslash|Q(t)|$ where each extremal region's cardinality, $|Q(t)|$ is a function of the given intensity threshold t and an intensity threshold increment Δ.

12. The architecture of claim 1 wherein the processing circuitry includes MSER selector hardware configured to automatically select MSERs based on the MSER criteria.

13. Architecture for maximally stable extremal regions (MSERs)-based detection of exudates in an ocular fundus comprising:
   a communication interface;
   memory;
   intensity image process hardware coupled to the memory and configured to receive a data stream through the communication interface of an ocular fundus image and store the pixels of the ocular fundus image within the memory and output labels to a first matrix within the memory for light image regions and dark image regions within the ocular fundus image for a given intensity threshold;
   extremal regions find hardware configured to receive the labels for the ocular fundus image and find MSERs within the ocular fundus image;
   MSER process hardware configured to receive MSER criteria that include a minimum MSER size in pixels and a maximum MSER size in pixels based upon an eye diameter size in pixels of the ocular fundus image and output through the communication interface a list of pixels for display based on the MSERs; and display hardware coupled to the communication interface for displaying highlighted pixels from the list of pixels for display.

14. The architecture of claim 13 wherein the intensity image process hardware is configured to substantially simultaneously provide the labels for the light image regions and the dark image regions within the ocular fundus image for the given intensity threshold.

15. The architecture of claim 13 wherein the intensity image process hardware is configured to provide the labels for the light image regions and the dark image regions within the ocular fundus image during a single processing pass for the given intensity threshold.

16. The architecture of claim 13 wherein the MSER criteria include a nested MSER tolerance value.

17. The architecture of claim 16 wherein the MSER criteria further include a minimum MSER area value, a maximum MSER area value, and an acceptable growth rate value for MSER areas.

18. The architecture of claim 13 wherein the MSER process hardware is further configured to determine MSER ellipses parameters that include a center of gravity, a major axis length, a minor axis length, and an angle of the major axis length with respect to a horizontal axis.

19. The architecture of claim 13 wherein the extremal regions find hardware is configured to find extremal regions using a mathematical relationship $q(t)=|Q(t+\Delta) \backslash Q(t-\Delta)|\backslash |Q(t)|$ where each extremal region's cardinality, $|Q(t)|$ is a function of an intensity threshold t and an intensity threshold increment $\Delta$.

20. The architecture of claim 13 wherein the intensity image process hardware includes union-find hardware configured to provide the labels for the light image regions and the dark image regions within the ocular fundus image for a given intensity threshold t.

21. The architecture of claim 20 wherein the intensity image process hardware further includes labeled region seeds updater/unifier hardware configured to prevent a seed that is a first pixel location within the ocular fundus image from being stored in a seed list if the seed is presently stored in the seed list.

22. The architecture of claim 21 further including region map updater hardware configured to store a value of $Q(t+\Delta)$, $Q(t)$, and $Q(t-\Delta)$ for each seed, where t is the intensity threshold and $\Delta$ is an increment of the intensity threshold t.

23. The architecture of claim 13 wherein the intensity image process hardware, the extremal regions find hardware, and the MSER process hardware are fabricated on a single application-specific integrated circuit.

24. The architecture of claim 13 wherein the intensity image process hardware, the extremal regions find hardware, and the MSER process hardware are implemented on a single field-programmable gate array.

25. A method for maximally stable extremal regions (MSERs)-based detection of exudates in an ocular fundus via processing circuitry with memory comprising:

receiving a data stream of an ocular fundus image via a communication interface in communication with the processing circuitry;

storing the ocular fundus image within the memory via the processing circuitry;

generating labels for light image regions and dark image regions within the ocular fundus image for a given intensity threshold t in real time via the processing circuitry;

storing the labels within the memory via the processing circuitry;

finding MSERs within the ocular fundus image based on the labels and MSER criteria in real time via the processing circuitry; and generating an MSER pixel list based on the MSERs and MSER criteria that include a minimum MSER size in pixels and a maximum MSER size in pixels based upon an eye diameter size in pixels of the ocular fundus image in real time via the processing circuitry;

providing for display through the communication interface via the processing circuitry the pixels of the ocular fundus image that are located within the MSER pixel list to indicate the exudates in the ocular fundus.

26. The method of claim 25 wherein generating the labels for the light image regions and generating labels for the dark image regions occurs substantially simultaneously.

27. The method of claim 25 wherein generating the labels for the light image regions and generating labels for the dark image regions occurs during a single processing pass for the given intensity threshold t.

28. The method of claim 25 wherein the MSER criteria include a nested MSER tolerance value.

29. The method of claim 28 wherein the MSER criteria further include a minimum MSER area, a maximum MSER area, and an acceptable growth rate value for MSER areas.

30. The method of claim 25 further including determining MSER ellipses parameters that include a center of gravity, a major axis length, a minor axis length, and an angle of the major axis length with respect to a horizontal axis via the processing circuitry.

31. The method of claim 25 wherein the processing circuitry includes MSER moments calculator hardware configured to calculate MSER moments.

32. The method of claim 31 wherein the processing circuitry further includes elliptical fit approximator hardware configured to receive the MSER moments from the MSER moments calculator hardware and fit an MSER ellipse to an extremal region based on the MSER moments.

33. The method of claim 25 wherein the processing circuitry includes union-find hardware configured to provide the labels for the light image regions and the dark image regions within the ocular fundus image that match the given intensity threshold t.

34. The method of claim 31 wherein the processing circuitry includes extremal region find hardware that is configured to receive the labels for the light image regions and the dark image regions and find extremal regions based on the labels for the light image regions and the dark image regions.

35. The method of claim 34 wherein the extremal region find hardware is configured to find extremal regions using a mathematical relationship $q(t)=|Q(t+\Delta)\backslash Q(t-\Delta)|/|Q(t)|$ where each extremal region's cardinality $|Q(t)|$ is a function of an intensity threshold t and an intensity threshold increment $\Delta$.

36. The method of claim 25 wherein the processing circuitry includes MSER selector hardware configured to automatically select the MSERs based on the MSER criteria.

* * * * *